United States Patent [19]

Tsutsu et al.

[11] Patent Number: 5,006,717
[45] Date of Patent: Apr. 9, 1991

[54] METHOD OF EVALUATING A SEMICONDUCTOR DEVICE AND AN APPARATUS FOR PERFORMING THE SAME

[75] Inventors: Noriko Tsutsu, Osaka; Yoshiro Nakata, Ikoma; Hideya Esaki, Toyonaka, all of Japan

[73] Assignee: Matsushita Electric Industrial Co., Ltd., Osaka, Japan

[21] Appl. No.: 456,994

[22] Filed: Dec. 26, 1989

[30] Foreign Application Priority Data

Dec. 26, 1988 [JP] Japan .............................. 63-328253

[51] Int. Cl.$^5$ ............................................. H05B 33/00
[52] U.S. Cl. .............................. 250/484.1; 250/458.1; 250/459.1; 358/106
[58] Field of Search ............... 250/484.1, 458.1, 549.1; 358/106

[56] References Cited

U.S. PATENT DOCUMENTS 4,680,635 7/1987 Khurana .............................. 358/211
4,755,874 7/1988 Esrig et al. .......................... 358/106

OTHER PUBLICATIONS

N. Khurane, et al., *Analysis of Product Hot Electron Problems by Gated Emission Microscopy*, IEEE/IRPS 189 (1986).

Takada et al., "An Empirical Model for Device Degradation due to Hot Courier Injection", *IEEE Electron Device Letters*, vol. EDL/4, No. 4, pp. 111-113, Apr. 1983.

Toriumi et al., "A Study of Photon Emission from N--channel MOSFET's", *IEEE, Trans. on Electron Devices*, vol. ED-34, No. 7, Jul. 1987.

*Primary Examiner*—Carolyn E. Fields
*Assistant Examiner*—James E. Beyer
*Attorney, Agent, or Firm*—Panitch Schwarze, Jacobs & Nadel

[57] ABSTRACT

A method and apparatus for evaluating the lifetime of a semiconductor device are disclosed. Luminescence of a predetermined wavelength which is emitted from an operating semiconductor device is detected. The luminescence of the predetermined wavelength is one which correlates with the degradation of the semiconductor device. Then, the image of detected luminescence of the predetermined wavelength is processed to determine the place of the degradation caused by hot carriers.

18 Claims, 10 Drawing Sheets

METHOD OF EVALUATING A SEMICONDUCTOR DEVICE AND AN APPARATUS FOR PERFORMING THE SAME

BACKGROUND OF THE INVENTION

1. Field of the Invention

The present invention relates to a method of evaluating a semiconductor device and an apparatus for performing the same, and more particularly, to a method and apparatus for evaluating the reliability or lifetime of a semiconductor device by analyzing weak luminescence emitted from the device.

2. Description of the Prior Art

With the miniaturization of semiconductor devices, it has been a major reliability problem that device characteristics are degraded when hot carriers generated by a high electric field created in an operating device are injected and caught in the gate oxide film thereof.

Heretofore, the lifetime of a semiconductor device considering degradation of characteristics due to hot carriers has been measured by actually applying a stress voltage to the semiconductor device. However, this measurement method requires a considerable period of time and a substantial number of samples. Furthermore, the application of the method is limited to the evaluation of individual transistors.

In recent years, there has been developed apparatuses which detect and visualize weak luminescence caused by hot carriers. In such an apparatus, the positions and amounts of luminescence within an integrated device such as an LSI are detected to evaluate the lifetime characteristics of the device affected by degradation of device characteristics. Examples of such an apparatus are Hot Electron Analyzer C3230 of Hamamatsu Photonics (Hamamatsu, Japan), and Insulating Film Destruction Detector EMMI of KLA Instrument Corporation (Calif., U.S.A.).

Figure 11:
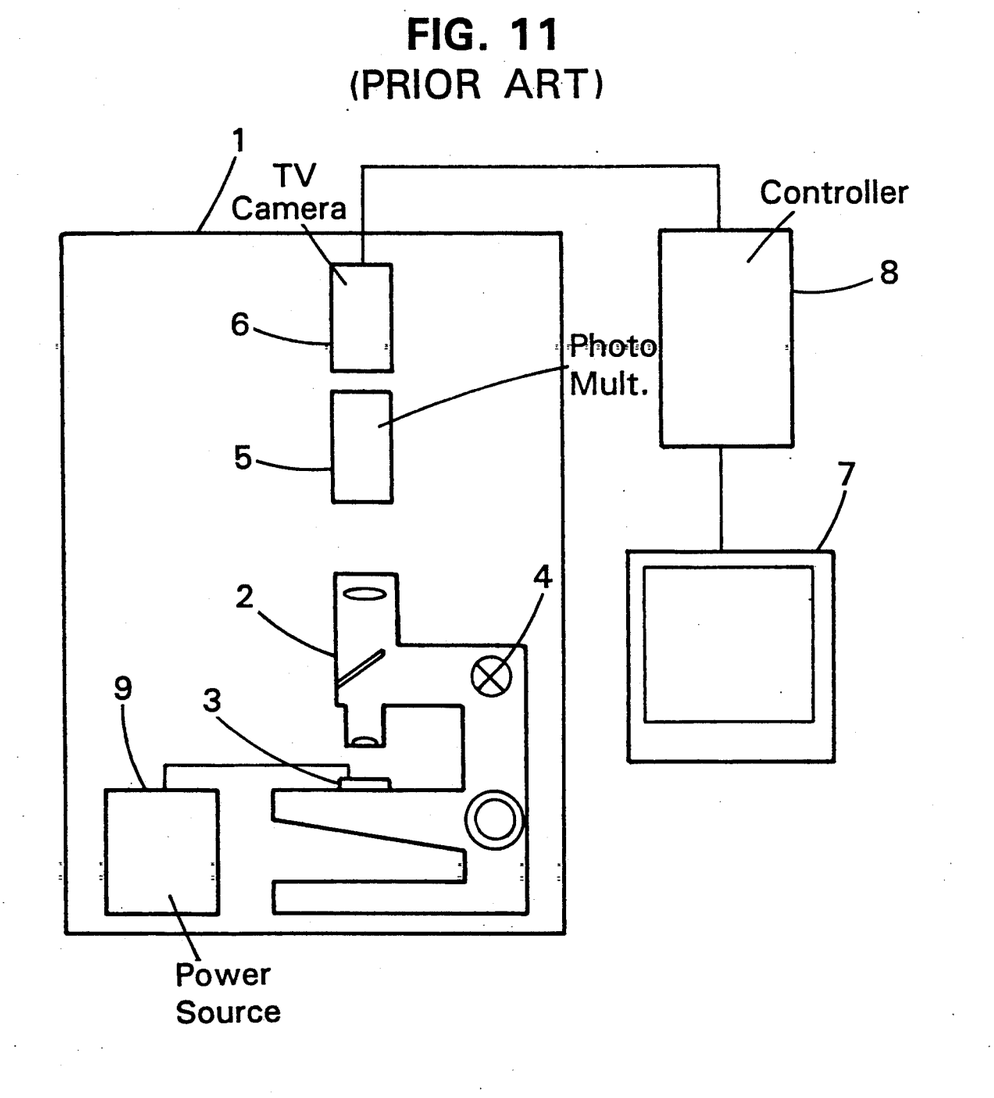
FIG. 11 shows schematically a conventional apparatus.

FIG. 11 illustrates the former apparatus. When evaluating the lifetime of a semiconductor device 3 by the apparatus of FIG. 11, the device 3 is mounted in a microscope 2 placed in a darkroom 1, and illuminated by a light source 4. The image of the device 3 enlarged by the microscope 2 is input to a TV camera 6 via a photomultiplier 5, and then displayed on a display 7. A controller 8 controls these units and stores this image from the TV camera 6 in its internal memory. Next, with shielding the semiconductor device 3 from light, a voltage of a predetermined level is applied to the device 3 from a power source 9. Weak luminescence emitted from the semiconductor device 3 is magnified through the microscope 2, and is then input to the photomultiplier 5. The intensity of the luminescence is multiplied to a visible level so that the luminescence image is picked up by the camera 6 to be displayed on the display 7, while the amount or intensity of the luminescence is accumulated as the form of the number of photons and stored in the internal memory of the controller 8 for a predetermined period of time. By superimposing the image obtained as a result of accumulating the luminescence over the previously stored image of the device 3 in the controller 8, it is possible to detect and measure the positions and distribution of the luminescence. Then, it is evaluated that a device with a greater amount of luminescence has a greater number of hot carriers generated, and therefore has a shorter lifetime because the device characteristics are degraded by hot carriers.

Figure 12:
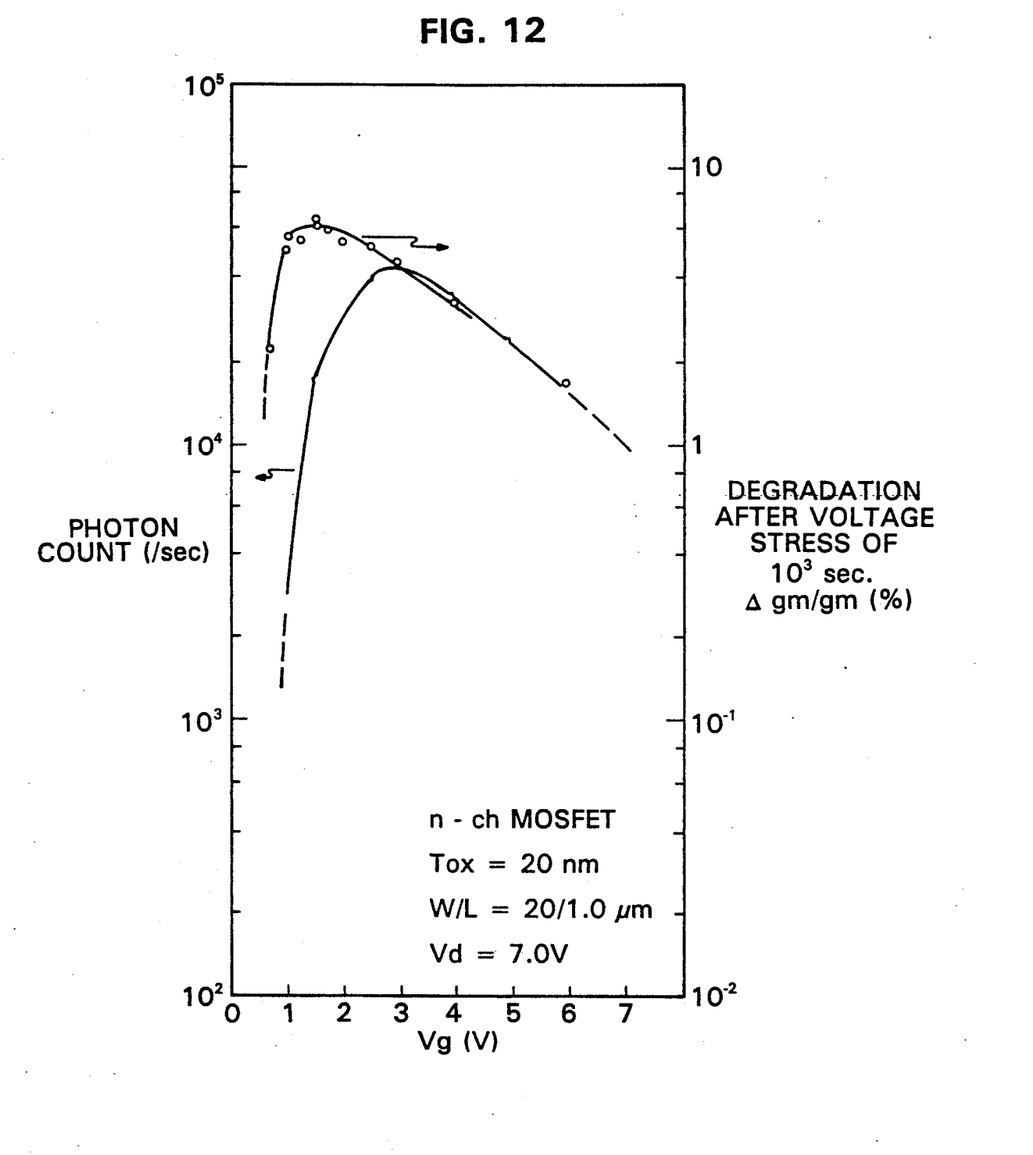
FIG. 12 is a graph showing characteristics of N-channel MOSFET obtained by the conventional apparatus.

However, the above-mentioned technique has drawbacks as described below. FIG. 12 shows the gate voltage dependence of the amount of luminescence measured by the conventional apparatus shown in FIG. 11 with regard to an N-channel MOSFET in which a prefixed drain voltage of 7 V is applied. FIG. 12 also shows the gate voltage dependence of a characteristic degradation rate $\Delta$ gm/gm after application of a voltage stress for $10^3$ sec which is obtained under the same condition. The results shown in FIG. 12 indicate that devices with greater amounts of light emission do not necessarily have a shorter lifetime due to the degradation of device characteristics, and that the peak of luminescence amount deviates from that of the device characteristic degradation. This means that it is not possible to accurately estimate the device life by evaluating the luminescence amount alone. Another problem with the conventional equipment is that, unless the wavelength distribution of the luminescence amount is taken into account, the measured luminescence amount has a value inherent in the system because corrections are not made with respect to factors such as the spectral sensitivity of the apparatus and the absorption of light as it passes through lenses.

SUMMARY OF THE INVENTION

The method of evaluating a semiconductor device of this invention, which overcomes the above-discussed and numerous other disadvantages and deficiencies of the prior art, comprises steps of: (a) operating the semiconductor device; and (b) detecting luminescence of a predetermined wavelength emitted from the operating semiconductor device, said luminescence of said predetermined wavelength being the one which best correlates with the degradation of the semiconductor device.

In a preferred embodiment, the predetermined wavelength is 500 nm or less, and said method further comprises a step of conducting the image processing of said detected luminescence to obtain the intensity of said detected luminescence.

The method of evaluating a semiconductor device of this invention comprises steps of: (a) operating the semiconductor device (b) detecting at least two kinds of luminescence of different predetermined wavelengths emitted from the operating semiconductor device (c) obtaining the intensity of each kind of said detected luminescence; and (d) calculating the intensity of luminescence of another wavelength which correlates with the degradation of the semiconductor device, using a predetermined expression and said obtained intensities.

In a preferred embodiment, the predetermined expression is the empirical formula $N = C_1 \cdot \exp(C_2 \cdot E)$, where E is the energy corresponding to a wavelength, N is the intensity per unit energy, and $C_1$ and $C_2$ are constants.

In a preferred embodiment, the other wavelength is one corresponding to energy which is greater than 3.2 eV.

In a preferred embodiment, the other wavelength is in the vicinity of 200 nm.

The method of evaluating a semiconductor device of this invention comprises steps of: (a) obtaining an image of the semiconductor device; (b) operating the semiconductor device (c) detecting a two-dimensional distribution of at least two kinds of luminescence of different predetermined wavelengths emitted from the operating semiconductor device; (d) calculating a two-dimensional distribution of luminescence of another wavelength which correlates with the degradation of the semiconductor device, from said detected two-dimensional distribution of said at least two kinds of luminescence, using a predetermined expression; and (e) comparing said calculated two-dimensional distribution with said image to determine a place where hot carriers are generated.

In a preferred embodiment, the predetermined expression is the empirical formula $N=C_1 \cdot \exp(C_2 \cdot E)$, where E is the energy corresponding to a wavelength, N is the intensity per unit energy, and $C_1$ and $C_2$ are constants.

In a preferred embodiment, the other wavelength is in the vicinity of 200 nm.

The apparatus for evaluating a semiconductor device of this invention comprises means for operating the semiconductor device, and means for detecting luminescence of a predetermined wavelength emitted from the operating semiconductor device, said luminescence of said predetermined wavelength being the one which correlates with the degradation of the semiconductor device.

In a preferred embodiment, the predetermined wavelength is 500 nm or less, and said apparatus further comprises: image processing means for processing said detected luminescence; and means for obtaining the intensity of said detected luminescence.

The apparatus for evaluating a semiconductor device comprises: means for operating the semiconductor device; means for detecting at least two kinds of luminescence of different predetermined wavelengths emitted from the operating semiconductor device; means for obtaining the intensity of each kind of said detected luminescence; and means for calculating the intensity of luminescence of another wavelength which correlates with the degradation of the semiconductor device, using a predetermined expression and said obtained intensities.

In a preferred embodiment, the predetermined expression is the empirical formula $N=C_1 \cdot \exp(C_2 \cdot E)$, where E is the energy corresponding to a wavelength, N is the intensity per unit energy, and $C_1$ and $C_2$ are constants.

In a preferred embodiment, the other wavelength is one corresponding to energy which is greater than 3.2 eV.

In a preferred embodiment, the other wavelength is in the vicinity of 200 nm.

The apparatus for evaluating a semiconductor device of this invention comprises: means for obtaining an image of the semiconductor device; means for operating the semiconductor device; means for detecting a two-dimensional distribution of at least two kinds of luminescence of different predetermined wavelengths emitted from the operating semiconductor device; means for calculating a two-dimensional distribution of luminescence of another wavelength which correlates with the degradation of the semiconductor device, from said detected two-dimensional distribution of said at least two kinds of luminescence, using a predetermined expression; and means for comparing said calculated two-dimensional distribution with said image to determine a place where hot carriers are generated.

In a preferred embodiment, the predetermined expression is the empirical formula $N=C_1 \cdot \exp(C_2 \cdot E)$, where E is the energy corresponding to a wavelength, N is the intensity per unit energy, and $C_1$ and $C_2$ are constants.

In a preferred embodiment, the other wavelength is in the vicinity of 200 nm.

Thus, the invention described herein makes possible the objectives of:

(1) providing a method of evaluating a semiconductor device which can accurately evaluate the lifetime of the device;

(2) providing a method of evaluating a semiconductor device which can accurately evaluate the degradation of the device;

(3) providing a method of evaluating a semiconductor device which is effective in analyzing the failure of the device;

(4) providing a method of evaluating a semiconductor device which is effective in evaluating the reliability of the device;

(5) providing an apparatus for evaluating a semiconductor device which can accurately evaluate the lifetime of the device;

(6) providing an apparatus for evaluating a semiconductor device which can accurately evaluate the degradation of the device;

(7) providing an apparatus for evaluating a semiconductor device which is effective in analyzing the failure of the device; and (8) providing an apparatus for evaluating a semiconductor device which is effective in evaluating the reliability of the device.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

The inventors have investigated spectra of luminescence caused by hot carriers and emitted from operating semiconductor devices, using the above-mentioned weak luminescence measuring apparatus and a wavelength filter or spectrometer, and found that, in the wavelength range of 400 to 800 nm, there is a closer correlation between the amount of luminescence and the degradation of device characteristics due to hot carriers, as the wavelength becomes shorter.

It is considered that a part of the energies of hot carriers generated by a high electric field in a semiconductor device is observed as luminescence. Therefore, it can be considered that the luminescence energy (wavelength) caused by hot carriers is the energy of hot carriers themselves. As the wavelength of the luminescence is shorter, the corresponding energy of hot carriers is greater. The degradation of semiconductor device characteristics due to hot carriers is caused when hot carriers having high energy are injected and caught in the gate oxide film of the semiconductor device. The energy corresponding to the wavelength of 400 nm is 3.1 eV, which is close to the barrier height of 3.2 eV at the Si-SiO$_2$ junction. Therefore, if it is assumed that the degradation of device characteristics is caused when hot carriers having energy of 3.2 eV or higher are injected and caught in the SiO$_2$ gate oxide film, the emission of a greater amount of light having a wavelength corresponding to 3.2 eV or higher energy results in a shorter lifetime of the device because it means a greater number of hot carriers having energy of 3.2 eV or higher, and thus a greater degree of degradation due to such hot carriers.

Accordingly, by examining the amount of luminescence having a wavelength (for example, a wavelength corresponding to 3.2 eV or higher energy) which most closely correlates with the device deterioration, it is possible to more accurately estimate the degree of device characteristic degradation and the lifetime of the device, which have not been possible to be correlated with each other by merely measuring the amount of luminescence.

The invention will be described in more detail by illustrating more specific embodiments.

EXAMPLE 1

Figure 1:
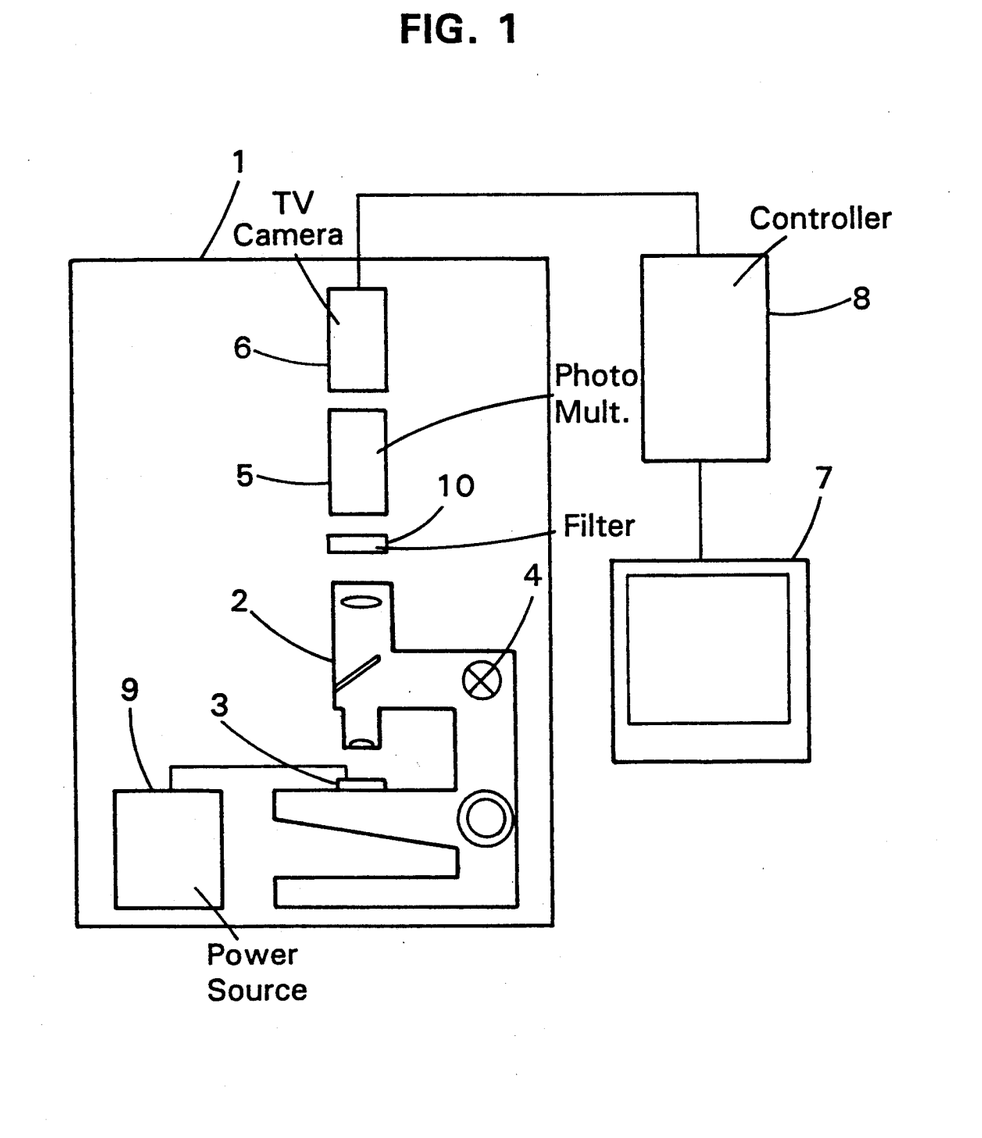
FIG. 1 shows schematically an apparatus according to the invention.

FIG. 1 shows an apparatus according to the invention. The apparatus of FIG. 1 comprises a darkroom 1, a microscope 2 disposed in the darkroom 1, a light source 4 for the microscope 2, a photomultiplier 5, a TV camera 6, a display 7, a controller 8, a power source 9, and a wavelength filter 10 which is detachably disposed in the system. A semiconductor device 3 such as an N-channel MOSFET to be evaluated is mounted in the microscope 2. First, while illuminating the device 3 with light from the light source 4, a magnified image of the device 3 is obtained by the microscope 2. In this case, the filter 10 is not used. The magnified image is further enlarged by the photomultiplier 5, and then sent to the TV camera 6 to be displayed on the display 7. The controller 8 controls these units and stores the image from the TV camera 6 in its internal memory. Next, while shielding the semiconductor device 3 from light from the light source 4 as well as from the outside, a voltage of a predetermined level is applied to the device 3 from the power source 9, and the luminescence emitted from the device 3 is magnified by the microscope 2, and is then input to the photomultiplier 5 through the wavelength filter 10. The luminescence image which has been greatly enlarged is picked up by the TV camera 6 and displayed on the display 7, while the luminescence is accumulated as the form of the number of photons in the internal memory of the controller 8 for a predetermined period of time. In the controller 8, the stored luminescence image is superimposed over the previously stored external image of the semiconductor device 3. The superimposed images are displayed on the display 7. Therefore, it is possible to detect and measure the positions and the distribution of the luminescence having the wavelength filtered by the wavelength filter 10.

Figure 2:
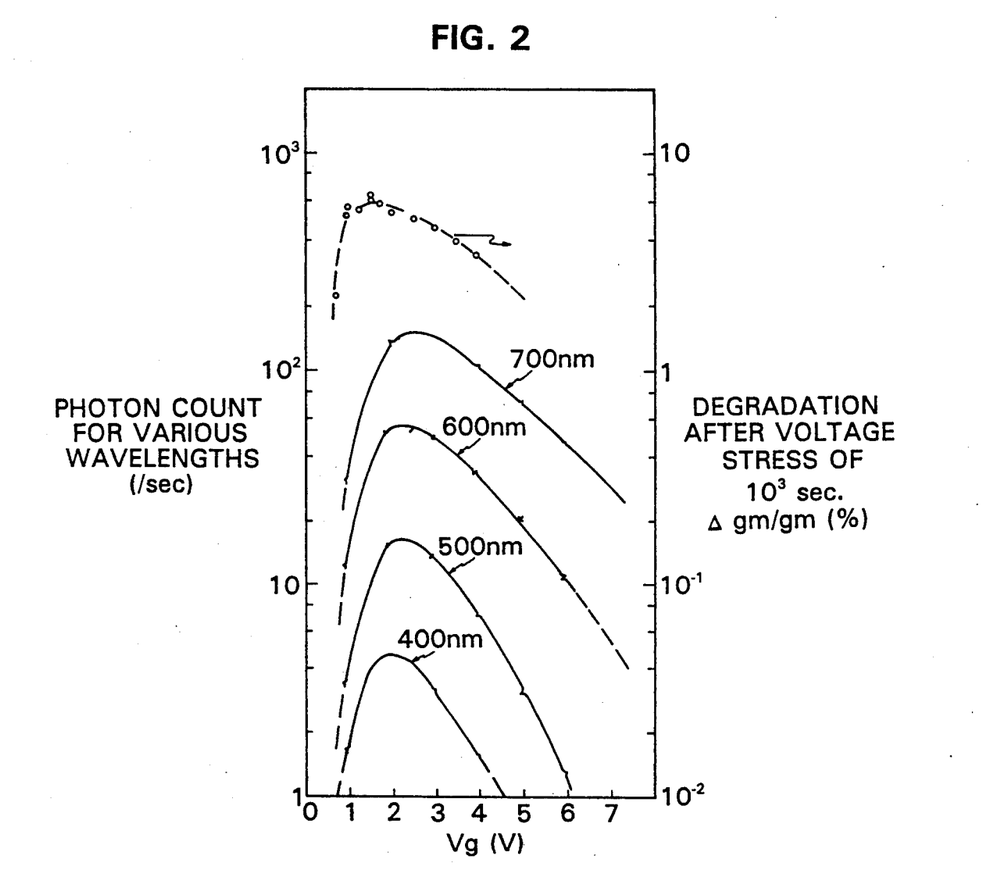
FIG. 2 is a graph showing characteristics of an N-channel MOSFET obtained by the apparatus of FIG. 1

In FIG. 2, the solid line shows the gate voltage dependence of the amount of luminescence obtained from measurements in which an N-channel MOSFET was examined with a predetermined drain voltage (7 V) applied thereto and using as the filter 10 band-pass filters having a full width of half maximum (FWHM) of 10 nm and center wavelengths of 400, 500, 600, and 700 nm, respectively. The gate voltage dependence of a characteristic deterioration rate $\Delta gm/gm$ after application of a stress voltage for $10^3$ sec. is shown by a broken line in FIG. 2. It can be seen that the peak of the luminescence amount approaches the peak of the degradation as the wavelength of the luminescence becomes shorter from 700 nm to 400 nm. Therefore, by using a wavelength filter of a wavelength range having the closest correlation with the device deterioration (e.g., a wavelength of 400 nm or shorter), it is possible to examine the luminescence of this wavelength range and to determine that semiconductor devices with greater amounts of luminescence in that range suffer greater degradation of device characteristics by hot carriers and therefore have a shorter lifetime.

It is desirable that the wavelength range of the wavelength filter used for the measurement should be determined, taking into account the spectral sensitivity of the apparatus, the spectral transmittance of lenses of the microscope and other instruments used for the measurement, the absorption by the poly-Si gate materials, etc. In short wavelengths of 400 nm and shorter, since the transmittance of optical lenses used in ordinary microscopes drops markedly, and also the amount of luminescence caused by hot carriers decreases, it tends to become difficult to detect luminescence. This problem can be effectively avoided by measuring luminescence having a wavelength of 500 nm or shorter or using fused quartz optical lenses which transmit light of the ultraviolet region.

As is apparent from FIG. 2, luminescence emitted from a semiconductor device increases as the wavelength becomes longer in the range of 400 nm to 700 nm. On the other hand, luminescence of a wavelength longer than 800 nm gives a smaller measured value because of the absorption by Si. This means that the prior art evaluation method in which no wavelength analysis is performed conducts only the measurement of luminescence in the vicinity of 700 nm. It is considered that this causes the difference between the device degradation and the amount of luminescence in the prior art technique.

EXAMPLE 2

Figure 3:
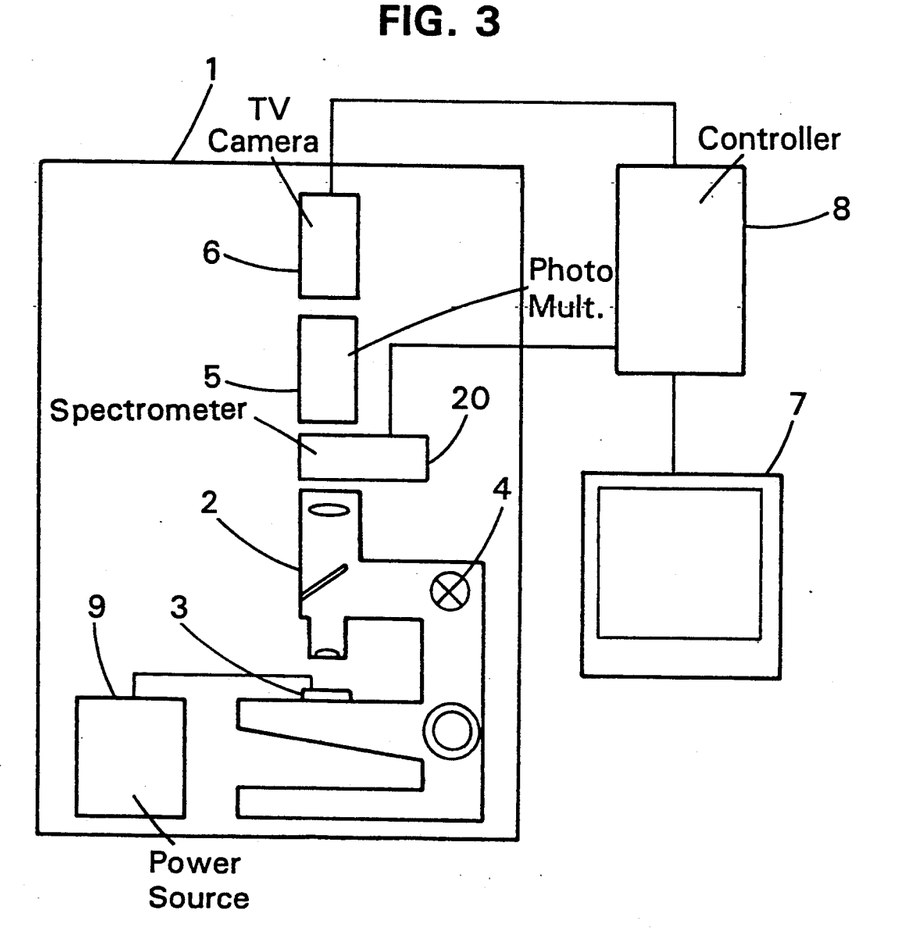
FIG. 3 shows schematically another apparatus according to the invention.

FIG. 3 shows another apparatus according to the invention. This embodiment differs from the first embodiment in that a spectrometer 20 is used instead of the wavelength filter 10. The measuring method is almost the same as in the first embodiment. Using the spectrometer 20, the amount of luminescence of a wavelength (for example, 400 nm and 500 nm) which most closely correlates with the device degradation is examined, and the life shortening degradation caused by hot carriers can be estimated. According to the embodiment, accurate data can be obtained more quickly by providing the controller 8 with a function to control the spectrometer 20.

EXAMPLE 3

First, an evaluation method for semiconductor devices according to a third embodiment will be described. In this embodiment, an apparatus similar to that used in the first or second embodiment can be used. As in the first or second embodiment, using a wavelength filter or a spectrometer, the amount of luminescence from a semiconductor device operated with a voltage applied thereto is measured with regard to at least two different wavelengths (for example, 500 nm and 700 nm). Next, from the measured data, the amount of light emission having a wavelength which is considered to most closely correlate with the device degradation (e.g., a wavelength corresponding to energy of 3.2 eV or more) is calculated based on the fact that energy E corresponding to each wavelength and the luminescence amount N per unit energy can be expressed by an empirical formula $N = C_1 \cdot \exp(C_2 \cdot E)$ (where $C_1$ and $C_2$ are constants). This relation is reported by Toriumi et al. (IEEE, Trans. Electron Devices, vol. ED-34, pp. 1501–1508, 1987). In accordance with the results of this calculation, it can be deduced that semiconductor devices having greater amounts of luminescence have a shorter lifetime because of greater degradation of the device characteristics.

The third embodiment will be described in more detail by using experimental data obtained by the inventors. Referring to FIG. 2, when the amount of luminescence of each wavelength is compared with the gate voltage dependence of the device degradation amount, the gate voltage at which the luminescence amount is at its peak approaches the gate voltage at which the degradation amount is at its peak, as the wavelength of luminescence becomes shorter from 700 nm to 400 nm, but at 400 nm, the peak of luminescence still does not agree with that of the degradation amount. It is considered that the peak of luminescence agrees with that of the degradation amount at a wavelength shorter than 400 nm. That is, it can be said that the closest correlation between the amount of luminescence and the amount of device degradation caused by hot carriers is established at a wavelength shorter than 400 nm.

However, it is difficult to directly measure the luminescence of a wavelength shorter than 400 nm, which is considered most closely correlated with deterioration, because the spectral sensitivity of the apparatus, the absorption through lenses, etc. causes the luminescence to be masked by noises.

Figure 4:
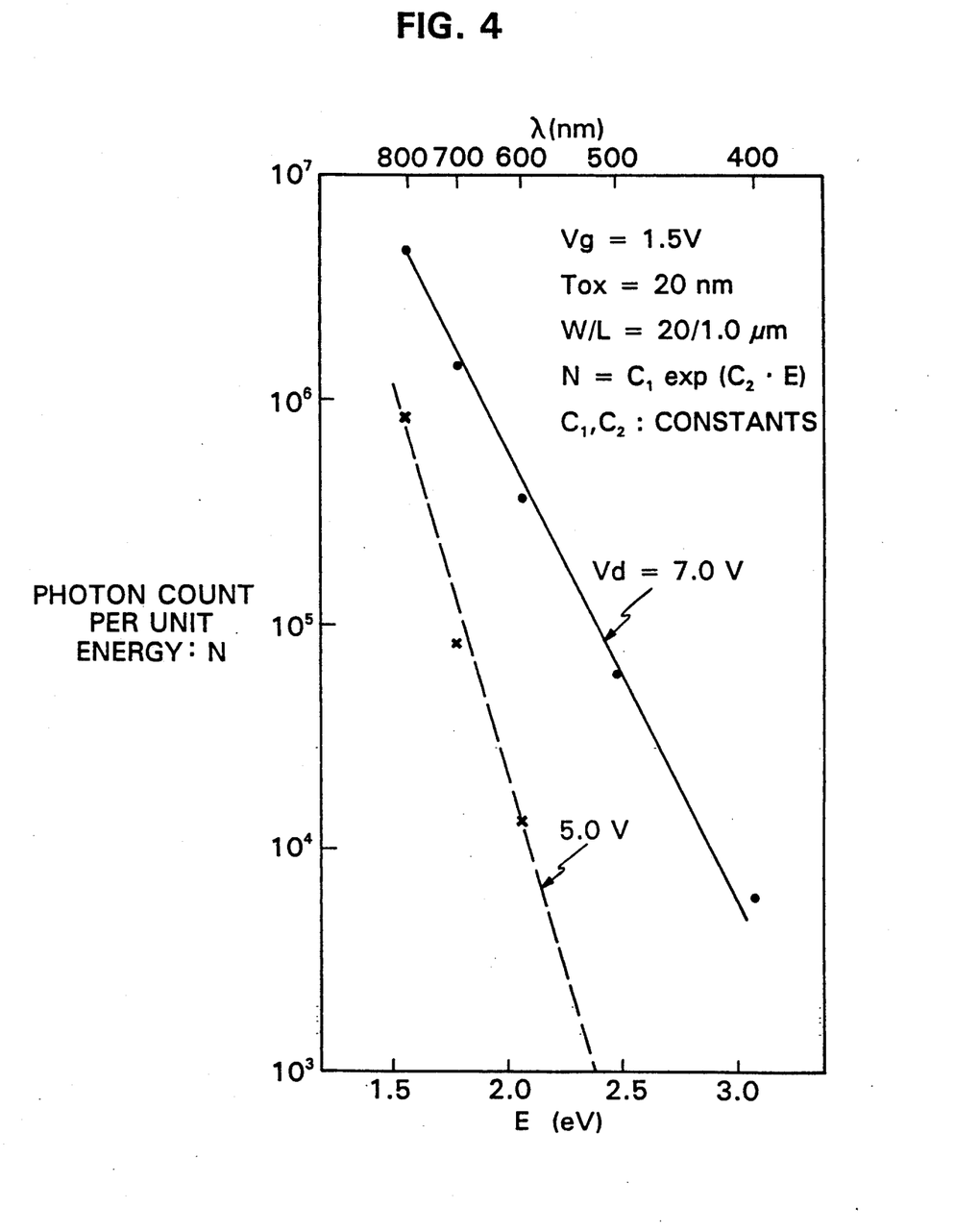
FIG. 4 is a graph showing the relationship between energy and photon counts per unit energy.

In the embodiment, therefore, a method in which the amount of luminescence of a wavelength shorter than 400 nm is obtained by calculation was employed. Using the apparatus of the first embodiment and band-pass filters having an FWHM of 10 nm and center wavelengths of 400, 500, 600, and 700 nm, respectively, the luminescence from an N-channel MOSFET to which a predetermined voltage (Vg = 1.5 V, Vd = 5 V and 7 V) was applied was examined with respect to each wavelength. Further, corrections were made to the luminescence amount of each wavelength with respect to the absorption by poly-Si, the transmittance of the lenses and wavelength filter, and the spectral sensitivity of the photomultiplier. FIG. 4 is a graph showing the relationship between the energy corresponding to each wavelength and the emission amount per unit energy. The solid line shows the relationship obtained when Vd = 7 V, and the broken line that obtained when Vd = 5 V. It can be seen from FIG. 4 that the relationship between the energy E corresponding to each wavelength and the luminescence amount N per unit energy can be expressed by the above-mentioned expression, $N = C_1 \cdot \exp(C_2 \cdot E)$. The slope of the graph can also change with gate and drain voltages other than those shown in FIG. 4, and it was confirmed that these changes also satisfy the above expression. From the above empirical formula, the constants $C_1$ and $C_2$ can be obtained by measuring the luminescence amounts of at least two different wavelengths, and by conducting further calculation, the luminescence amount having any given wavelength can be obtained.

Therefore, by obtaining from the above empirical formula the luminescence amount having the wavelength considered most closely correlated with the device deterioration (for example, the wavelength corresponding to 3.2 eV or higher energy), it can be deduced that semiconductor devices having greater amounts of luminescence have shorter lifetime because of the greater device degradation caused by hot carriers.

Figure 5:
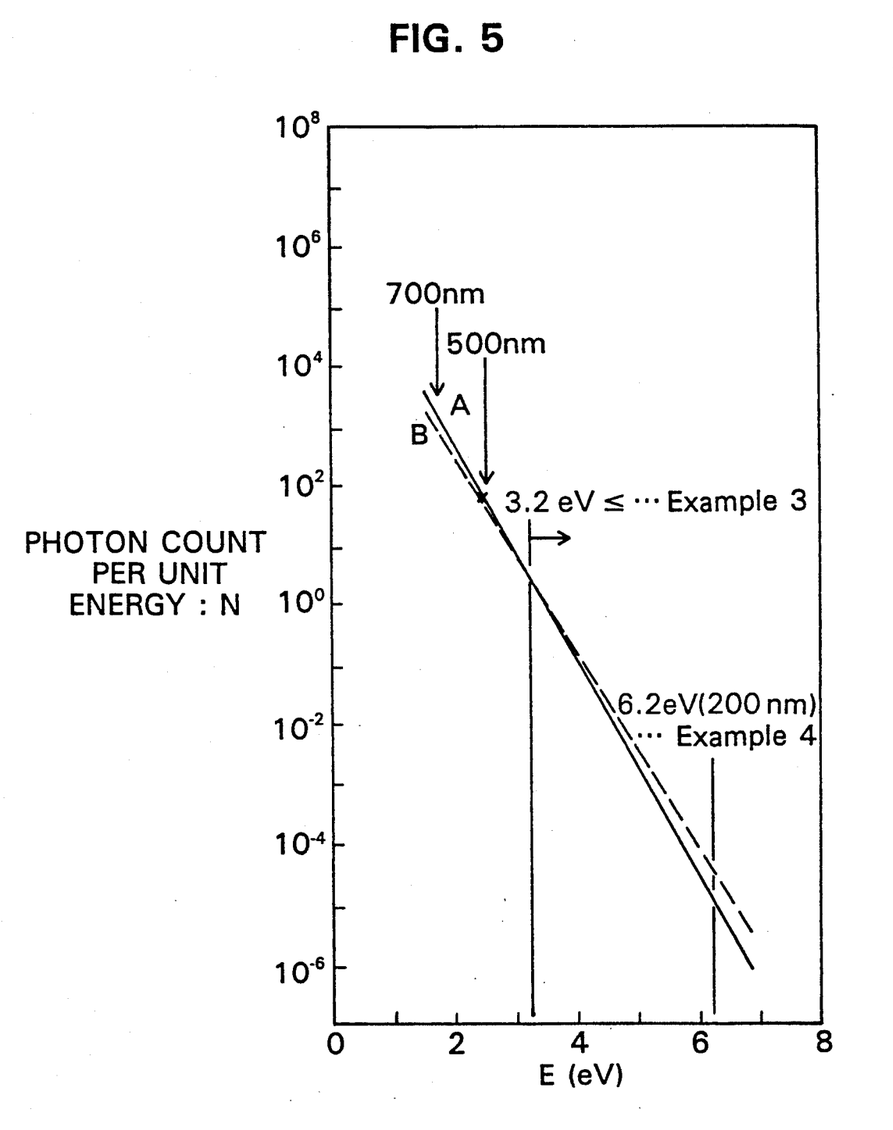
FIG. 5 is a graph showing the relationship between photon counts per unit energy and energy corresponding to 500 nm and 700 nm.

Using band-pass filters having an FWHM of 10 nm and center wavelengths of 500 nm and 700 nm, two N-channel MOSFETs A and B in which luminescence had been observed during operation were examined to check the amount of the luminescence of each wavelength. The results are shown in FIG. 5. The solid line shows the results obtained from the MOSFET A, and the broken line those obtained from the MOSFET B. According to the measured results, the MOSFET A has a greater luminescence amount when measured without a filter and at a wavelength of 700 nm, while at 500 nm, both the MOSFETs A and B show almost the same luminescence amount. On the other hand, when the amount of luminescence having a wavelength corresponding to 3.2 eV or higher energy considered most closely correlated with device degradation was obtained from the above empirical formula, it was found that the MOSFET B has a greater amount of luminescence, as shown in FIG. 5. In FIG. 5, because the ordinate is plotted in logarithmic form, the difference between A and B appears slight, but actually, the difference is several times greater than it appears.

Then, we conducted a circuit operation analysis on each of the MOSFETs A and B using an EB tester, to find that the drain voltage was almost the same, i.e. 5 V, in both transistors, while the gate voltage was approximately 3 V in the MOSFET A, and approximately 2 V in the MOSFET B, indicating that the MOSFET B was subjected in bias conditions which cause greater device degradation by hot carriers. This proves that the evaluation according to the embodiment is effective in practice in the evaluation of the degradation of semiconductor devices caused by hot carriers. It was also found from the above results that with the prior art evaluation technique in which the wavelength analysis of luminescence is not conducted, the MOSFET A may be detected to have a greater luminescence amount, and therefore, it is not possible to accurately estimate the degradation of characteristics caused by hot carriers. As previously mentioned, this is because in the prior art technique, measurement is made with respect to light emission of longer wavelength, i.e. in the vicinity of 700 nm.

EXAMPLE 4

Figure 6:
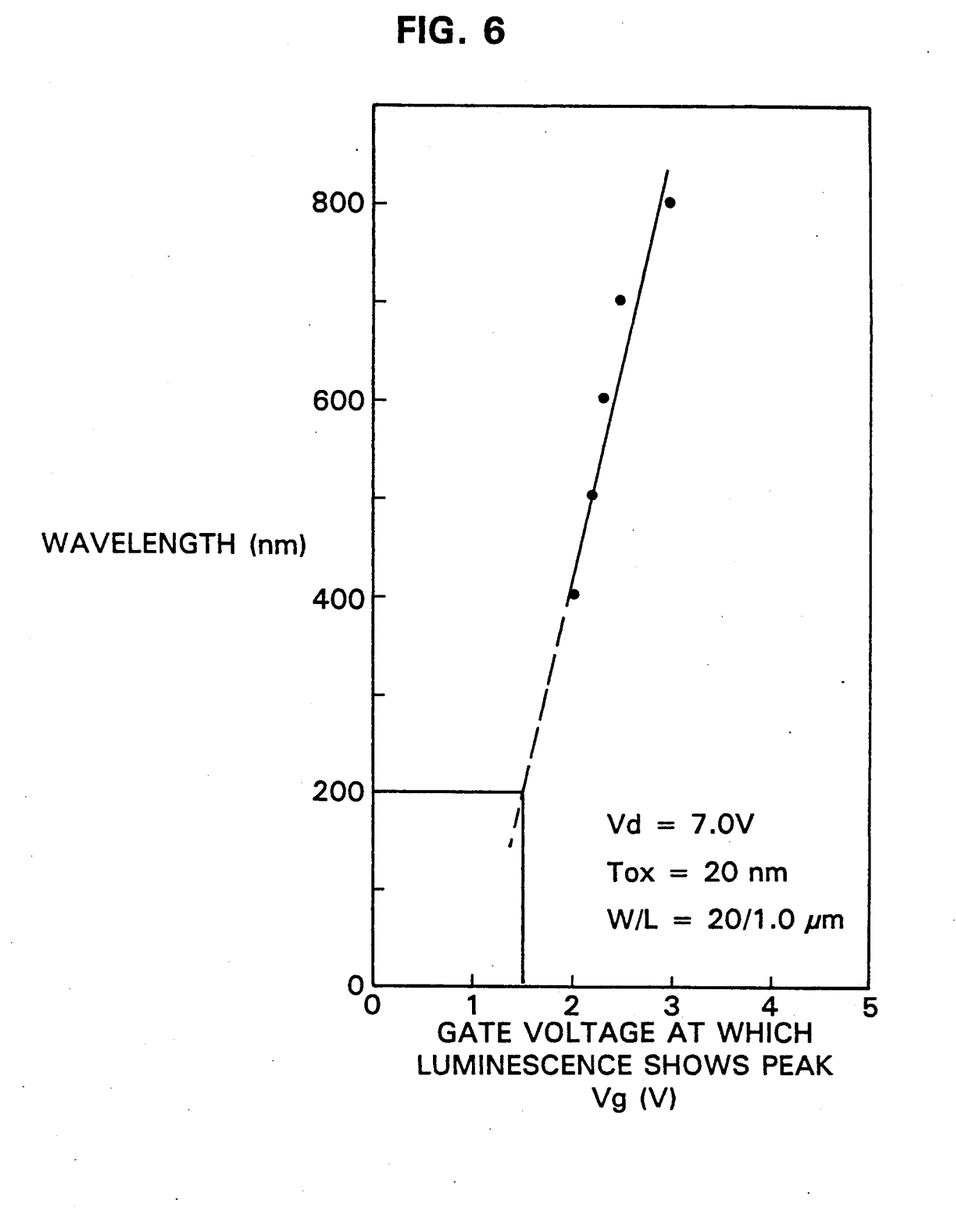
FIG. 6 is a graph showing the relationship between the wavelength of luminescence and the gate voltage at which luminescence is at peak.

From the relationship between the luminescence of each wavelength and the gate voltage shown in FIG. 2, the relationship between the wavelength of luminescence and the gate voltage at which the luminescence of that wavelength is at its peak is noted and represented in the form of a graph shown in FIG. 6. As shown in FIG. 6, the peak of the luminescence amount approaches the peak of the degradation amount as the wavelength of the luminescence becomes shorter from 700 nm to 400 nm, and at the gate voltage of 1.5 V at which the degradation amount is at its peak, it is deduced that the luminescence having a wavelength of approximately 200 nm has its peak.

Figure 7:
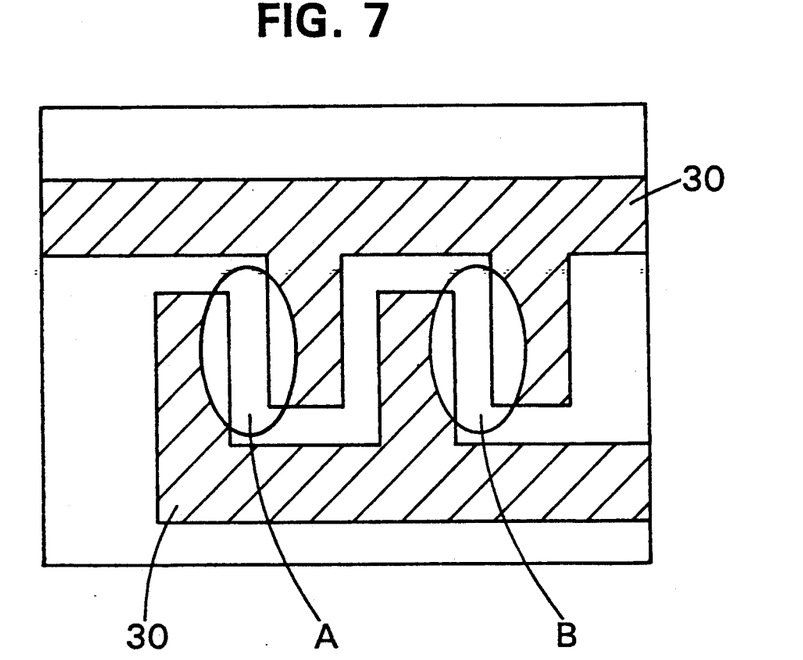
FIG. 7 shows schematically a partial plan view of a semiconductor device.
Figure 8:
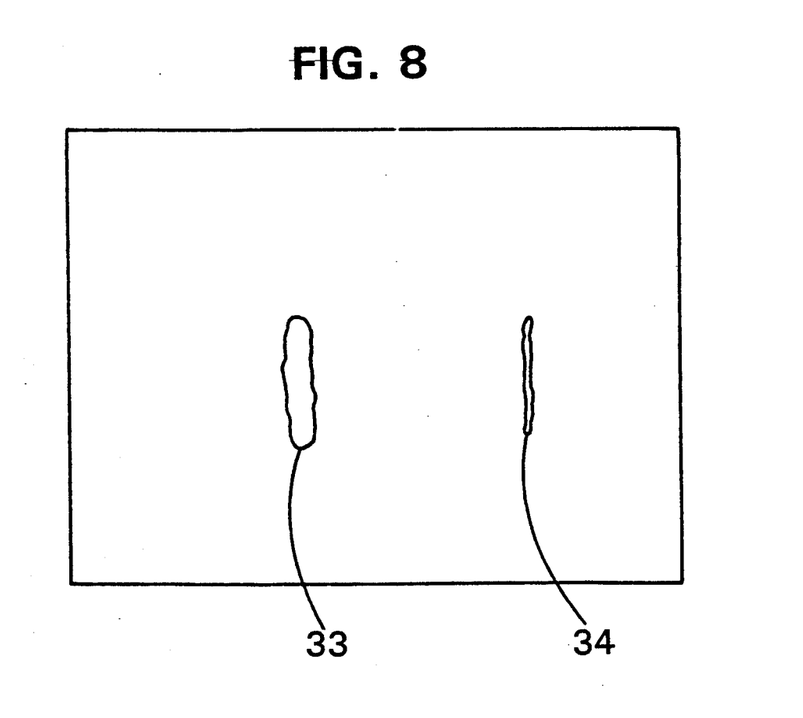
FIG. 8 is a diagram illustrating the luminescence image of the device of FIG. 7 obtained when a bandpass filter of 700 nm is used.
Figure 9:
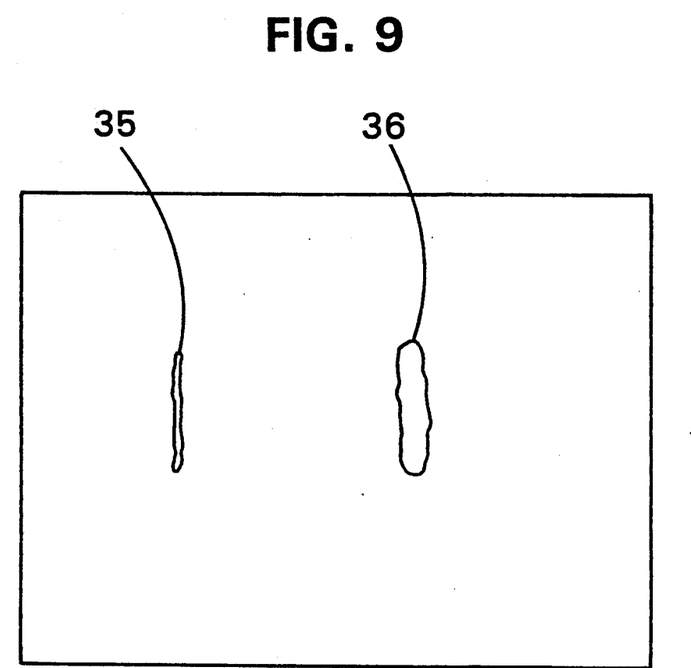
FIG. 9 is a diagram illustrating the calculated two-dimensional distribution of luminescence of 200 nm.

In the similar manner in the first or second embodiment, the image of a semiconductor device and the two-dimensional distribution of luminescence of at least two different wavelengths (for example, 500 nm and 700 nm) were measured. The obtained data was stored in the controller B. FIG. 7 shows schematically an image of the semiconductor device. In FIG. 7, Al wirings 30 only are indicated, and the MOSFETs A and B are respectively formed at the encircled portions. FIG. 8 shows the stored image of two-dimensional distribution of luminescence obtained through a band-pass filter having a center wavelength of 700 nm and an FWHM of 10 nm. In FIG. 8, the numerals 33 and 34 indicate luminescence images of 700 nm which were obtained from the MOSFETs A and B, respectively. The stored images of two-dimensional distribution of luminescence obtained through a bandpass filter having a center wavelength of 500 nm and an FWHM of 10 nm are measured in the same manner. The images of two-dimensional distribution of luminescence were stored in the controller 8 in such a manner that the amount of luminescence of each pixel of the image was stored in the form of a numeric value. Next, using the previously mentioned empirical formula, $N = C_1 \cdot \exp(C_2 \cdot E)$, the luminescence amount of each pixel of the image in the wavelength of 200 nm is calculated from two-dimensional distribution data of 500 nm and 700 nm luminescence which has been stored in the controller 8. FIG. 9 shows schematically the two-dimensional distribution of the amount of 200 nm luminescence obtained from the calculation. The numerals 35 and 36 indicate images of 200 nm luminescence of the MOSFETs A and B, respectively. The controller 8 superimposed the image shown in FIG. 9 over that shown in FIG. 7.

Figure 10:
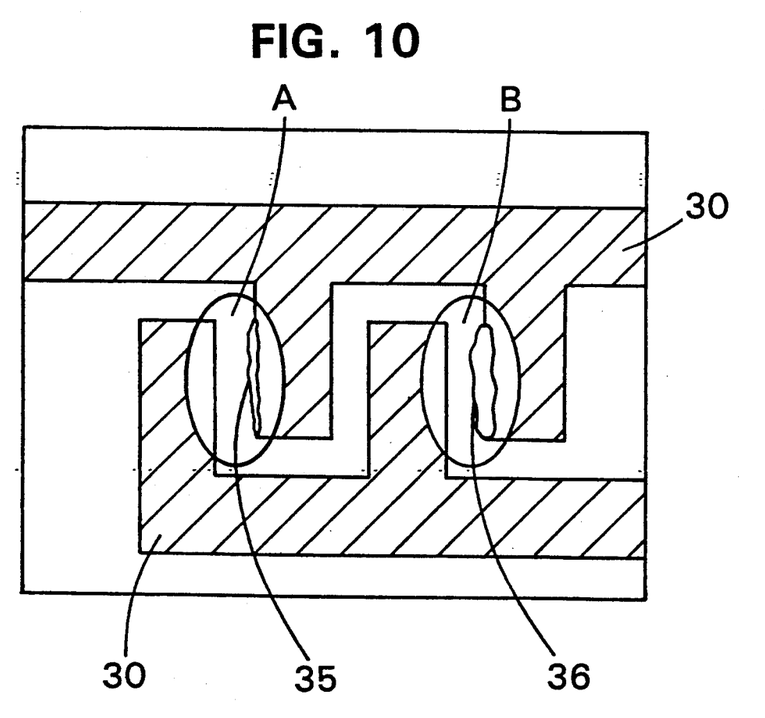
FIG. 10 is a diagram obtained by superposing the images of FIGS. 7 and 9.

FIG. 10 is a diagram showing the two-dimensional distribution of the luminescence amount (FIG. 9) superimposed over the image of the semiconductor device stored in the controller 8 (FIG. 7). FIG. 10 gives a quick view of the positions in the semiconductor device generating luminescence of a wavelength of 200 nm considered most closely correlated with degradation, thus making it possible to easily locate the place where the degradation of the device characteristics is caused by hot carriers which contribute to the shortening of the device lifetime.

When the amount of luminescence having a wavelength of 200 nm was calculated with regard to the two transistors A and B as described in the third embodiment, the transistor B was found to have a greater amount of luminescence, thus proving that the technique of this embodiment is also effective in practice for the evaluation of semiconductor device characteristics with regard to the degradation due to hot carriers.

According to the present invention, the amount of luminescence having a wavelength most closely correlated with the device degradation can be detected out of weak luminescence emitted from an operating semiconductor device, or is calculated from measured data, thereby making it possible to more accurately estimate the device life and/or degradation characteristics for which is has not been possible to establish a correlation by merely measuring the amount of luminescence. Thus, the evaluation efficiency for semiconductor devices is greatly enhanced. Therefore, the present invention provides a highly effective method and apparatus for failure analysis and reliability evaluation of semiconductor devices.

it is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method of evaluating a semiconductor device comprising steps of:
   (a) operating the semiconductor device; and
   (b) detecting luminescence of a predetermined wavelength emitted from the operating semiconductor device, said luminescence of said predetermined wavelength being the one which best correlates with the degradation of the semiconductor device.

2. A method according to claim 1, wherein said predetermined wavelength is 500 nm or less, and said method further comprises a step:
   (c) conducting the image processing of the detected luminescence to obtain the intensity of said detected luminescence.

3. A method of evaluating a semiconductor device comprising steps of:
   (a) operating the semiconductor device;
   (b) detecting at least two kinds of luminescence of different predetermined wavelengths emitted from the operating semiconductor device;
   (c) obtaining the intensity of each kind of the detected luminescence; and
   (d) calculating the intensity of luminescence of another wavelength which correlates with the degradation of the semiconductor device, using a predetermined expression and the obtained intensities.

4. A method according to claim 3, wherein said predetermined expression is the empirical formula $N = C_1 \cdot \exp(C_2 \cdot E)$, where E is the energy corresponding to a wavelength, N is the intensity per unit energy, and $C_1$ and $C_2$ are constants.

5. A method according to claim 3, wherein said another wavelength is one corresponding to energy which is greater than 3.2 eV.

6. A method according to claim 3, wherein said another wavelength is in the vicinity of 200 nm.

7. A method of evaluating a semiconductor device comprising steps of:
   (a) obtaining an image of the semiconductor device;
   (b) operating the semiconductor device;
   (c) detecting a two-dimensional distribution of at least two kinds of luminescence of different predetermined wavelengths emitted from the operating semiconductor device;

(d) calculating a two-dimensional distribution of luminescence of another wavelength which correlates with the degradation of the semiconductor device, from the detected two-dimensional distribution of said at least two kinds of luminescence, using a predetermined expression; and (e) comparing the calculated two-dimensional distribution with said image to determined a place where hot carriers are generated.

8. A method according to claim 7, wherein said predetermined expression is the empirical formula $N = C_1 \cdot \exp(C_2 \cdot E)$, where E is the energy corresponding to a wavelength, N is the intensity per unit energy, and $C_1$ and $C_2$ are constants.

9. A method according to claim 7, wherein said another wavelength is in the vicinity of 200 nm.

10. An apparatus for evaluating a semiconductor device comprising:
   means for operating the semiconductor device; and
   means for detecting luminescence of a predetermined wavelength emitted from the operating semiconductor device, said luminescence of said predetermined wavelength being the one which correlates with the degradation of the semiconductor device.

11. An apparatus according to claim 10, wherein said predetermined wavelength is 500 nm or less, and said apparatus further comprises:
   image processing means for processing the detected luminescence; and
   means for obtaining the intensity of said detected luminescence.

12. An apparatus for evaluating a semiconductor device comprising:
   means for operating the semiconductor device;
   means for detecting at least two kinds of luminescence of different predetermined wavelengths emitted from the operating semiconductor device;
   means for obtaining the intensity of each kind of the detected luminescence; and
   means for calculating the intensity of luminescence of another wavelength which correlates with the degradation of the semiconductor device, using a predetermined expression and the obtained intensities.

13. An apparatus according to claim 12, wherein said predetermined expression is the empirical formula $N = C_1 \cdot \exp(C_2 \cdot E)$, where E is the energy corresponding to a wavelength, N is the intensity per unit energy, and $C_1$ and $C_2$ are constants.

14. An apparatus according to claim 12, wherein said another wavelength is one corresponding to energy which is greater than 3.2 eV.

15. An apparatus according to claim 12, wherein said another wavelength is in the vicinity of 200 nm.

16. An apparatus for evaluating a semiconductor device comprising:
   means for obtaining an image of the semiconductor device;
   means for operating the semiconductor device;
   means for detecting a two-dimensional distribution of at least two kinds of luminescence of different predetermined wavelengths emitted from the operating semiconductor device;
   means for calculating a two-dimensional distribution of luminescence of another wavelength which correlates with the degradation of the semiconductor device, from the detected two-dimensional distribution of said at least two kinds of luminescence, using a predetermined expression; and means for comparing said calculated two-dimensional distribution with said image to determine a place where hot carriers are generated.

17. An apparatus according to claim 16, wherein said predetermined expression is the empirical formula $N = C_1 \cdot \exp(C_2 \cdot E)$, where E is the energy corresponding to a wavelength, N is the intensity per unit energy, and $C_1$ and $C_2$ are constants.

18. An apparatus according to claim 16, wherein said another wavelength is in the vicinity of 200 nm.

* * * * *